United States Patent [19]

McCaughan

[11] Patent Number: 4,719,237
[45] Date of Patent: Jan. 12, 1988

[54] CARDIAC ANTIARRYTHMIC METHOD EMPLOYING PROBUCOL

[75] Inventor: Donald McCaughan, Groveland, Mass.

[73] Assignee: Merrell Dow Pharmaceuticals Inc., Cincinnati, Ohio

[21] Appl. No.: 823,551

[22] Filed: Jan. 28, 1986

[51] Int. Cl.$^4$ .............................................. A61K 31/10
[52] U.S. Cl. ...................................... 514/712; 514/821
[58] Field of Search ................................ 514/712, 821

[56] References Cited

U.S. PATENT DOCUMENTS

| | | | |
|---|---|---|---|
| T960,003 | 7/1977 | Innes et al. | 514/706 |
| 3,862,332 | 1/1975 | Barnhart et al. | 514/712 |
| 4,451,260 | 5/1984 | Mitra | 424/21 |

FOREIGN PATENT DOCUMENTS 55-9041  1/1980  Japan ................... 514/712

OTHER PUBLICATIONS

Chem. Abst. 79:49264j (1973)–Marshall et al.
Chem. Abst. 96:28406t (1981)–Miettinen et al.
Chem. Abst. 101:481m (1984)–Browne et al.
Chem. Abst. 103:172,042b (1985)–Gershbein et al.
Erfahrungen mit Probucol bei einmal, Therapiewoche 35, 29 (1985).
Abstract from oral presentation, R. Weiss, et al, 5th Dresden Lipid Symposium, Int'l Symposium on Lipoproteins & Atherosclerosis, Dresden, Jun. 12–14, 1985. Oral presentation abs-Racted in Item 2 and its English translation.
G. Troendle, et al., Lancet, May 22, 1982, p. 1179.
D. McCaughan, Lancet, Jul. 16, 1982, p. 161.
B. L. Martz, Lancet, Jun. 12, 1982, p. 1365.
D. McCaughan, Artery 10(1), 56 (1982).
R. E. Tedeschi, et al., Artery 10(1), 22 (1982).
T. A. Miettinen, et al., Artery 10(1), 35 (1982).
Physicians' Desk Reference, 41st edition, Medical Economics Company, Inc., 1987, pp. 1357–1359.

*Primary Examiner*—Douglas W. Robinson
*Attorney, Agent, or Firm*—Stephen L. Nesbitt

[57] ABSTRACT

A method useful for alleviating cardiac arrhythmias such as tachycardias in animals by administering to arrhythmic animals an antiarrhythmic amount of 4,4'-(isopropylidenedithio)bis (2,6-di-t-butylphenol), probucol.

1 Claim, No Drawings

CARDIAC ANTIARRYTHMIC METHOD EMPLOYING PROBUCOL

BACKGROUND OF THE INVENTION

The compound of this invention 4,4'-(isopropylidenedithio)bis (2,6-di-t-butylphenol), probucol, is well-known and is currently used as an anticholesterolemic agents. It has now been discovered that probucol is a useful antiarrhythmic agent.

SUMMARY OF THE INVENTION

Probucol, 4,4'-(isopropylidenedithio)bis (2,6-di-t-butylphenol), when administered to animals suffering from cardiac arrhymias, is effective.

DETAILED DESCRIPTION OF THE INVENTION

In accordance with the invention an antiarrhythmic amount of probucol is administered to an arrhythmic animal. The terms "arrhythmic" and "arrhythmia" as employed herein refer to irregular cardiac activity characterized by irregular beating of the heart, that is, non-rhythmic heartbeat. Such arrhythmias involve substantial departures from the regular, normal sinus heartbeat. Arrhythmias are generally far beyond the normal increased, but still substantially regular, heartbeat rate resulting from physical activity. The term is inclusive of the conditions described by terms such as ventricular fibrillation, ventricular tachycardia, atrioventricular nodal beats, auricular flutter, auricular fibrillation or premature ventricular contractions. The term "arrhythmic animal," as employed in the present specification and claims, means and refers to an animal suffering cardiac arrhythmias. Such arrhythmias can be the result of physiological or pathological conditions, can be brought about by physical conditions such as electrical stimulation or physical injury or they can be brought about by pharmacological effects such as the administration of compounds such as digitalis or similar compounds such as ouabain, acetyl strophanthidin, deslanatoside C or digitoxin; epinephrine; ergot; chloroform; and cyclopropane having cardiac stimulant and arrhythmia-inducing activity or side effects.

In the practice of the invention, probucol is normally incorporated in a pharmaceutical carrier and the resulting composition is administered internally to an arrhythmic animal. In the present specification and claims, "pharmaceutical carrier" refers to known pharmaceutical excipients which are substantially non-toxic and non-sensitizing at dosage levels consistent with good antiarrhythmic activity. Probucol is preferably administered both parenterally in the form of liquid injectable solutions or suspensions, and orally in the form of liquid compositions or solid compositions. Suitable pharmaceutical carriers which can be employed for formulating the solid compositions such as for tablets or capsules include starch, lactose, glucose, sucrose, gelatin, powdered licorice, malt, rice flour, chalk, silica gel, hydroxyethyl cellulose, sodium alginate, hydroxypropyl cellulose, magnesium carbonate, and magnesium stearate and compatible mixtures thereof. Probucol can also be formulated as liquid compositions including syrups, elixirs, suspensions and emulsions for oral administration. Among the liquid pharmaceutical carriers which can be employed for orally-administered compositions are ethanol, water, saline, glucose syrup, syrup of acacia, mucilage of tragacanth, propylene glycol, polyethylene glycols, peanut oil, wheat germ oil, sunflower seed oil or corn oil and the like and compatible mixtures thereof. Orally-ingestible emulsions are prepared with the aid of emulsifying agents such as lecithin, sorbitan trioleate, polyoxyethylene sorbitan monoleate and natural gums such as gum acacia and gum tragacanth.

Suspensions are prepared with the aid of suspending agents such as polyethylene oxide condensation products of alkylphenols or fatty acids or fatty alcohols, or cellulose derivatives such as carboxymethyl cellulose or hydroxypropylmethyl cellulose. The compositions can also contain sweetening agents such as calcium cyclamate or calcium saccharin, flavoring agents such as caramel or licorice, coloring materials, and preservatives.

Injectable compositions adapted for parenteral administration such as intramuscular, subcutaneous or, preferably, intravenous injection can be prepared with carriers such as water, normal saline solutions, Ringer's Injection, Lactated Ringer's Injection, dextrose solutions, ethanol, propylene glycol, liquid polyethylene glycols, fixed vegetable oils such as corn oil, peanut oil or cottonseed oil, ethyl oleate, and isopropyl myristate. The injectable compositions can also contain other materials such as preservatives and buffers. The selection of the exact pharmaceutical carrier to be employed in any given circumstance can be carried out by routine and conventional range finding operations to arrive at formulations having the desired characteristics of physical form, ease of administration in a desired route, storage stability, and the like.

The antiarrhythmic amount of probucol to be administered to an arrhythmic animal can vary depending upon such factors as the severity of the arrhythmia exhibited, the cause of the arrhythmia, the method and frequency of administration, the exact antiarrhythmic effect to be produced and the species, size, weight, age and physical condition of the particular animal being treated. In general, when the animal is actively exhibiting arrhythmia, it is preferred to administer probucol at an antiarrhythmic dosage rate sufficient to bring about a complete conversion of the arrhythmia to normal sinus cardiac activity. In such operations, probucol is preferably introduced directly into the cardiovascular system of the animal to provide an antiarrhythmic concentration thereof in the blood sufficient to alleviate the arrhythmia. In a convenient procedure probucol is administered by intravenous injection at an initial antiarrhythmic dosage less than that required to fully convert the arrhythmia to normal rhythm, and the heartbeat of the animal is monitored as the amount of compound administered is gradually increased over a period of minutes until an antiarrhythmic amount sufficient to fully convert the arrhythmia to rhythmic cardiac activity has been administered. It is then preferred to supply probucol in periodic maintenance antiarrhythmic dosages, such administration being either by the same parenteral route, or by administration of larger antiarrhythmic dosages by another route such as by oral administration. The maintenance antiarrhythmic dosage and mode of administration are selected to provide a more-or-less continuous antiarrhythmic concentration of probucol in the cardiovascular system, such concentration being sufficient to inhibit further arrhythmia. In general, probucol can be administered intravenously in initial dosages of from about 500or less to about 10,000 or more micrograms per kilogram of animal body weight, providing antiarrhythmic concentrations in the cardiovascular system of about 40 or lower to about 800 or more micrograms per liter of blood. Maintenance dosages can vary widely depending upon a variety of factors such as the time and frequency of administration, the condition, size, age and species of the animal, the route of administration selected, the type of dosage form employed, the type and cause of the arrhythmia, and the length of time during which a maintenance dose is desired. In cases in which there is little or no likelihood of recurrence of arrhythmia once conversion has been brought about, the maintenance dosage can comprise a continuation of the initial intravenous antiarrhythmic dosage for a relatively brief period. Maintenance dosages can be administered by single or multiple doses provided that probucol is administered in an amount sufficient to provide an antiarrhythmic concentration of probucol in the blood or to provide alleviation of cardiac arrhythmia. When the active ingredient is administered orally as in the form of tablets or capsules, it is preferred to employ compositions in dosage unit form containing the mixed compound in an amount between about 50 and about 200 milligrams per unit. When probucol is administered by procedures such as intravenous injection or infusion, it is preferred to employ sterile injectable liquid compositions in dosage unit form containing from about 10 to about 100 milligrams of the mixed ether compound per unit, the units comprising about 1 to about 10 milliliters of total liquid.

In general, the compositions of the invention contain from about 2 to about 95 percent probucol in a pharmaceutical carrier.

The preparation of probucol is well known in the art. For example probucol can be prepraed by dissolving 2,6-di-tert-butyl-4-mercaptophenol (47.5 g, 0.2 mol) in methanol (50 ml) heated to 50° C. A catalytic amount of concentrated hydrochloric acid (1 milliliter) is added, followed by acetone (5.8 grams; 0.1 mole). The temperature of the mixture rises to about 60° C., and is maintained at about 60°-65° C. for 1.5 hours. The mixture is cooled, diluted with water and about 10 milliliters of aqueous sodium bicarbonate and extracted with ether. The ether extract is evaporated, and the product is obtained as a residue, which is recrystallized from ethanol and then from isopropanol to obtain probucol as a crystalline solid melting at about 125°-126° C.

In another representative procedure about 2.3 moles of 2,6-di-tert-butyl-4-mercaptophenol is dissolved in about 1700 milliliters of methanol under a nitrogen atmosphere; about 100 milliliters of concentrated hydrochloric acid and 180 milliliters of acetone are added, and the mixture is stirred and maintained at a temperature of about 35°-50° C. for 1.5 hours. The mixture is then cooled to room temperature and filtered, and the probucol is collected as a colorless crystalline solid filler cake. The product is washed with water and aqueous sodium bicarbonate and purified by recrystallization from methanol.

EXAMPLE 1

150 grams of 4,4'-(isopropylidenedithio)bis(2,6-di-t-butylphenol) are intimately mixed with 50 grams of magnesium stearate, 305 grams of gum acacia and 1145 grams of corn starch and the mixture is compressed into slugs. The slugs are broken into granules which are passed through a twelve to fourteen mesh screen and mixed with an additional 50 grams of magnesium stearate. The mixture is then compressed into tablets weighing 0.55 gram each.

EXAMPLE 2

Twenty milliliters of ethanol are diluted with 80 milliliters of polyethylene glycol-200 to make a total of 100 milliliters of liquid. Two grams of 4,4'-(isopropylidenedithio)bis(2,6-di-t-butylphenol) are dissolved in the ethanol-polyethylene glycol-200 mixture and the solution sterilized. There is thus obtained a composition suitable for intravenous injection for the purpose of lowering serum cholesterol. Injection of 5 milliliters of the composition supplies 100 milligrams of the active ingredient.

EXAMPLE 3

Tablets are prepared from a granulation comprising 250 parts by weight of 4,4'-(isopropylidenedithio)-bis(2,6-di-t-butylphenol), 50 parts lactose, 3.5 parts magnesium stearate, 20 parts starch, 50 parts microcrystalline cellulose, one part of polyoxyethylene sorbitan monooleate surface active dispersing agent and 0.4 part of F.D. and C. approved color. The granulation is screened and compressed into tablets weighing about 0.287 gram each to prepare a composition in dosage unit form adapted for oral administration to animals.

EXAMPLE 4

250 parts by weight of 4,4'-(isopropylidenedithio)-bis(2,6-di-t-butylphenol) is dispersed in a mixture of 385 parts by weight of diethylsuccinate. 125 parts by weight of ethyl linoleate and 125 parts by weight of a surface active dispersing agent (polyoxyethylene sorbitan monooleate). The mixture is filled into soft gelatin capsules in the amount of 0.76 milliliter per capsule to obtain a dosage unit form containing about 0.250 gram of probucol.

I claim:

1. A method for treating cardiac arrhythmias which comprises administering to an animal in need thereof a therapeutically effective amount of the compound probucol.

* * * * *